United States Patent
Knothe Tate (10) Patent No.: US 11,814,757 B2
(45) Date of Patent: Nov. 14, 2023

(54) ENGINEERED MATERIALS AND METHODS OF FORMING

(71) Applicants: Melissa Knothe Tate, Wentworth Falls (AU); BIOCONIX PTY LTD., Wentworth Falls (AU)

(72) Inventor: Melissa Knothe Tate, Wentworth Falls (AU)

(73) Assignee: BIOCONIX PTY LTD., Wentworth Falls (AU)

(*) Notice: Subject to any disclaimer, the term of this patent is extended or adjusted under 35 U.S.C. 154(b) by 1200 days.

(21) Appl. No.: 15/757,948

(22) PCT Filed: Jun. 15, 2016

(86) PCT No.: PCT/IB2016/053553
§ 371 (c)(1),
(2) Date: Mar. 6, 2018

(87) PCT Pub. No.: WO2016/203409
PCT Pub. Date: Dec. 22, 2016

(65) Prior Publication Data
US 2018/0230626 A1    Aug. 16, 2018

Related U.S. Application Data

(60) Provisional application No. 62/175,842, filed on Jun. 15, 2015.

(51) Int. Cl.
*A61L 27/36* (2006.01)
*D03C 19/00* (2006.01)
(Continued)

(52) U.S. Cl.
CPC .......... *D03C 19/005* (2013.01); *A61L 27/227* (2013.01); *A61L 27/24* (2013.01);
(Continued)

(58) Field of Classification Search
CPC ..... D03C 19/005; D03C 3/20; A61L 27/3633; A61L 27/227; A61L 27/24;
(Continued)

(56) References Cited

U.S. PATENT DOCUMENTS 5,085,252 A    2/1992  Mohamed et al.
5,465,760 A    11/1995 Mohamed et al.
(Continued)

FOREIGN PATENT DOCUMENTS

WO    94/25080         11/1994
WO    1995/025482 A1    9/1995
(Continued)

OTHER PUBLICATIONS

Schenke-Layland, K. et al., Non-invasive multiphoton imaging of extracellular matrix structures, 2008, Journal of Biophotonics, 1(6), 451-462 (Year: 2008).*

(Continued)

*Primary Examiner* — Louise W Humphrey
*Assistant Examiner* — Anjali Ajit Hirani
(74) *Attorney, Agent, or Firm* — TAROLLI, SUNDHEIM, COVELL & TUMMINO L.L.P.

(57) ABSTRACT

A method of forming a substrate includes mapping a three dimensional spatial distribution of at least one structural protein fiber of extracellular matrix of biological material of interest, designing a fiber assembly pattern based on an intrinsic pattern of the at least one structural protein fiber of the extracellular matrix of the biological material, and assembling fibers based on the fiber assembly pattern to form the substrate.

15 Claims, 7 Drawing Sheets a Ovine model     b Sheep femur     c Histological processing and sectioning     d Transverse section of c (51) Int. Cl.
    *A61L 27/22*     (2006.01)
    *A61L 27/24*     (2006.01)
    *D03C 3/20*     (2006.01)
    *D03D 1/00*     (2006.01)
    *D03D 11/00*     (2006.01)
    *D03D 25/00*     (2006.01)
    *D03D 41/00*     (2006.01)

(52) U.S. Cl.
    CPC ....... *A61L 27/3633* (2013.01); *A61L 27/3641* (2013.01); *D03C 3/20* (2013.01); *D03D 1/00* (2013.01); *D03D 11/00* (2013.01); *D03D 25/005* (2013.01); *D03D 41/004* (2013.01); *A61L 2430/20* (2013.01); *D10B 2211/06* (2013.01); *D10B 2403/033* (2013.01); *D10B 2509/00* (2013.01)

(58) Field of Classification Search
    CPC ... A61L 27/3641; A61L 2430/20; D03D 1/00; D03D 11/00; D03D 25/005; D03D 41/004; D03D 2700/0174; D10B 2211/06; D10B 2403/033; D10B 2509/00; B33Y 80/00
See application file for complete search history.

(56) References Cited

U.S. PATENT DOCUMENTS

| | | |
|---|---|---|
| 5,709,854 A | 1/1998 | Griffith-Cima et al. |
| 6,208,886 B1 | 3/2001 | Alfano et al. |
| 2003/0003135 A1 | 1/2003 | Leung et al. |
| 2007/0041952 A1* | 2/2007 | Guilak ................ A61L 27/3654 424/93.7 |

FOREIGN PATENT DOCUMENTS

| | | |
|---|---|---|
| WO | 01/38662 A1 | 5/2001 |
| WO | 02/07961 A1 | 1/2002 |
| WO | 2006/045135 A1 | 5/2006 |
| WO | 2014/126876 A1 | 8/2014 |

OTHER PUBLICATIONS

Liao et al., "Composite Three-Dimensional Woven Scaffolds with Interpenetrating Network Hydrogels to Create Functional Synthetic Articular Cartilage", Adv. (2013) 23: 5833-5839.

Evans et al., "Solid-supported lipid bilayers to drive stem cell fate and tissue architecture using periosteum derived progenitor cells", Biomaterials, vol. 34, Issue 8, Mar. 2013, pp. 1878-1887.

Australian Examination Report for Application No. 2016280242 dated Aug. 28, 2020.

* cited by examiner

Fig. 3I a  Ovine model      b  Sheep       c  Histological      d  Transverse
                       femur          processing           section of c
                                      and sectioning

Figs. 4A-D e  High-resolution   f  xyz stack   g  3D render of      h  Reassembled
   imaging                             image sequence       virtual tissue

Figs. 4E-H i Segmentation, post-processing and virtual testing to create, optimize weaving algorithm for function. Collagen fiber distribution shown above j Computer-controlled weaving of fabric k Testing, optimization of novel periosteum-inspired, functional textile

Figs. 4I-K

ENGINEERED MATERIALS AND METHODS OF FORMING

RELATED APPLICATION

This application claims priority from U.S. Provisional Application No. 62/175,842, filed Jun. 15, 2015, the subject matter of which is incorporated herein by reference in its entirety.

BACKGROUND

Many disease conditions or injuries of the body require the repair or replacement of damaged tissues and/or structures, but the body itself may not be able to replace or repair the tissue and/or structures satisfactorily or within an appropriate time scale. Accordingly, many methods of disease or injury treatment involve augmenting the body's natural repair mechanisms and often rely on the use of implantable biological scaffolds or prostheses. Tissue engineering attempts to create three-dimensional tissue structures on which cells and other biomolecules can be incorporated.

Most previous tissue engineering approaches have utilized scaffolds comprised of highly porous meshes or hydrogels that are relatively isotropic and thus cannot provide the complex multidirectional and nonlinear properties believed necessary for sustained load support in vivo (Soltz, M. A., Ateshian, G. A. (2000) J. Biomech. Engng. 122:576). Traditional textile reinforced composites are made with 2-dimensional (2-D) woven fabrics. Ordinary 2-D weaving processes mechanically interlock yarns perpendicularly to each other by bending or crimping, significantly reducing each fiber's strength and subsequently, the reinforcement properties of the fabric. Additionally, composite parts, which require substantial thickness or complex shapes, must be made from multiple layers of fabric and/or fabrics cut and sewn to create the desired geometry.

SUMMARY

Embodiments describe herein relate to engineered materials whose structure is based on structural protein components of extracellular matrix of biological materials of, for example, animals and plants, as well as methods of forming the engineered materials. The engineered materials can replicate or mimic a biological material's or nature's intrinsic architecture of structural molecules, such as proteins, to provide mechanically functional textiles, including engineered tissue fabrics and tissue implants, and materials for transport and safety industries.

In some embodiments, a method of forming a substrate or textile of an engineered material, such as a biomedical material, tissue implant, or mechanically functional textile, can include mapping a three dimensional spatial distribution of at least one structural protein fiber and/or natural or synthetic analogs thereof of extracellular matrix of biological material of interest. A fiber assembly pattern can then be designed based on an intrinsic pattern of the at least one structural protein fiber and/or natural or synthetic analogs thereof of the extracellular matrix of the biological material. Fibers used to form the substrate can then be assembled based on the fiber assembly pattern.

In some embodiments, the at least one structural protein fiber comprises collagen fibers, elastin fibers, and/or natural or synthetic analogs thereof of the extracellular matrix of the biological material.

In other embodiments, the three dimensional spatial distribution of the collagen fibers and elastin fiber can be mapped using multimodal imaging techniques. For example, the three dimensional spatial distribution of the collagen fibers, the elastin fibers, and/or natural or synthetic analogs thereof can be mapped using, respectively, second harmonic imaging microscopy imaging and two photon excitation microscopy.

In some embodiments, the fiber assembly pattern can include a weaving algorithm or weaving motif based on the intrinsic pattern. The fibers can be assembled by weaving using the weaving algorithm to define a weave pattern and fiber orientation.

In other embodiments, the biological material that is mapped can include tissue of a plant or animal. The tissue can include at least one of periosteum, pericardium, perimycium, or tissue bounding an organ or tissue compartment.

Still other embodiments relate to a method of forming an engineered tissue construct. The method includes mapping a three dimensional spatial distribution of collagen fibers, elastin fibers, and/or natural or synthetic analogs thereof of the extracellular matrix of a tissue of interest. A fiber weaving motif is then designed based on an intrinsic pattern of the collagen fibers and elastin fibers of the extracellular matrix of the tissue. The fibers are weaved based on the fiberweaving motif to define the weave pattern and fiber orientation and form the engineered tissue construct.

In some embodiments, the engineered tissue construct can further include at least one bioactive agent incorporated on or within the woven fibers. The at least one bioactive agent can be capable modulating a function and/or characteristic of a cell. The bioactive material can include, for example, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-$\beta$ I-III)), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

In other embodiments, the engineered tissue construct can include at least one cell dispersed on the woven fibers. The cell can be, for example, a progenitor cell, such as totipotent stem cells, pluripotent stem cells, and multipotent stem cells, as well as any of their lineage descendant cells, including more differentiated cells. Exemplary progenitor cells can be selected from, but not restricted to, totipotent stem cells, pluripotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells are selected from, but not restricted to, de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

BRIEF DESCRIPTION OF THE DRAWINGS

FIGS. 2(A-G) illustrates periosteum as an interface between bone and muscle. (A) Transverse section of ovine femur diaphysis (B: bone, P: periosteum, M: muscle, black squares indicate regions of interest, ROI, along the major (1,2) and minor (3,4) centroidal axes of bone). Periosteum and bone are 'velcroed' together by Sharpey's fibers (B): outlined image of collagen arrangement making up two Sharpey's fibers) that anchor the soft tissue sleeve to the hard surface of bone through a multitude of connections that distributed force without concentrating stresses. In turn, periosteum and muscle are physically connected by higher order architectures including springs and struts interwoven between the two. (C) A 6×4 tiled image of the periosteum (P) bounded by bone (B) and skeletal muscle (M, muscle fascicles in cross section). Second harmonic signal from collagen fibers (arrows), shown in green; elastin signal shown in orange; Procion Red (PR) tracer delineating vascularization. ROI (white square) enlarged (D) to better visualize elastin fibers (arrows) and projected in 3D (E) from z-stack with 0.5 µm spacing in the z-direction. (F) Direct attachment of muscle, via struts, to the periosteum (arrows), and (G) blood vessel (BV) transecting the periosteum (P).

FIGS. 3(A-I) are a 3D rendering of z-stacks (depth circa 40 µm) of SHG/collagen channel to STL files. 3D modeling of SHIM (C) together with TPEM and procion red channels comprising (D) weak collagen, (E) strong collagen, (F) vascularization, (G) weak elastin, (H) strong elastin signals, combined in (I), where xyz voxel size is 0.48 µm×0.48 µm×0.5 µm.

FIGS. 4(A-K) are a schematic diagram illustrating the process for bottom-up weaving of multidimensional, natural tissue-inspired fabrics. (A-D) A transverse section of an ovine femur mid-diaphysis, with periosteum and surrounding muscle intact, stained with procion red solution. (E-F) Acquisition of high resolution z-stacks using paired SHIM and TPEM imaging protocols to visualize structural proteins including collagen and elastin. (G-I) 3D rendering of z-stacks to convert image sequence into STL files for 3D computational modeling. (J) Conversion of virtual model into a physical model using multidimensional weaving technology; periosteum-inspired fabric shown above, right. (K) Optimization of novel functional textile via mechanical testing.

DETAILED DESCRIPTION

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law tradition, the terms "a", "an", and "the" are meant to refer to one or more as used herein, including the claims. For example, the phrase "a cell" can refer to one or more cells.

The term "absorbable" is meant to refer to a material that tends to be absorbed by a biological system into which it is implanted. Representative absorbable fiber materials include, but are not limited to polyglycolic acid (PGA), polylactic acid (PLA), polyglycolide-lactide, polycaprolactone, polydioxanone, polyoxalate, a polyanhydride, a poly (phosphoester), catgut suture, collagen, silk, chitin, chitosan, hydroxyapatite, bioabsorbable calcium phosphate, hyaluronic acid, and any other medically acceptable yet absorbable fiber. Other absorbable materials include collagen, gelatin, a blood derivative, plasma, synovial fluid, serum, fibrin, hyaluronic acid, a proteoglycan, elastin, and combinations thereof.

The term "non-absorbable" is meant to refer to a material that tends not to be absorbed by a biological system into which it is implanted. Representative non-absorbable fiber materials include but are not limited to polypropylene, polyester, polytetrafluoroethylene (PTFE) such as that sold under the registered trademark TEFLON (E.I. DuPont de Nemours & Co., Wilmington, Del., United States of America), expanded PTFE (ePTFE), polyethylene, polyurethane, polyamide, nylon, polyetheretherketone (PEEK), polysulfone, a cellulosic, fiberglass, an acrylic, tantalum, polyvinyl alcohol, carbon, ceramic, a metal (e.g., titanium, stainless steel), and any other medically acceptable yet non-absorbable fiber.

The terms "anisotropic", "anisotropy", and grammatical variations thereof, refer to properties of a textile and/or fiber system as disclosed herein that can vary along a particular direction. Thus, the fiber and/or textile can be stronger and/or stiffer in one direction versus another. In some embodiments, this can be accomplished by changing fibers (such as, but not limited to providing fibers of different materials) in warp versus weft directions, and/or in the Z direction, for example. Thus, anisotropic characteristics parallel native properties of a tissue, and it is desirable to match or approximate one or more native properties of the tissue in the implantable composition.

Thus, strength can be provided in the direction needed and indeed it is possible to restore properties of a tissue almost immediately without necessarily needing for cells to grow into functional tissues. However, in some embodiments cells are provided and the growth into functional tissues is also provided.

The terms "anisotropic", "anisotropy" and grammatical variations thereof, can also include, but is not limited to the provision of more fiber in a predetermined direction. This can thus include a change of diameter in a fiber over a length of the fiber, a change in diameter at each end of the fiber, and/or a change in diameter at any point or section of the fiber; a change in cross-sectional shape of the fiber; a change in density or number of fibers in a volumetric section of the scaffold; and the use of monofilament fibers and/or multifilament fibers in a volumetric section of the textile; and can even include the variation in material from fiber system to fiber system and along individual fibers in a volumetric section of the textile.

The terms "biocompatible" and "medically acceptable" are used synonymously herein and are meant to refer to a material that is compatible with a biological system, such as that of a subject having a tissue to be repaired, restored, and/or replaced. Thus, the term "biocompatible" is meant to refer to a material that can be implanted internally in a subject as described herein.

The term "composite material", as used herein, is meant to refer to any material comprising two or more components. One of the components of the material can optionally comprise a matrix for carrying cells, such as a gel matrix or resin.

The term "bioactive agent" can refer to any agent capable of promoting tissue formation, destruction, and/or targeting a specific disease state (e.g., cancer). Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III)), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

The term "bioresorbable" can refer to the ability of a material to be fully resorbed in vivo. "Full" can mean that no significant extracellular fragments remain. The resorption process can involve elimination of the original implant material(s) through the action of body fluids, enzymes, cells, and the like.

The term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Exemplary progenitor cells can be selected from, but not restricted to, totipotent stem cells, pluripotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells are selected from, but not restricted to, de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

The term "effective amount" refers to an amount of a bioactive agent sufficient to produce a measurable response (e.g., a biologically relevant response in a cell exposed to the differentiation-inducing agent) in the cell. In some embodiments, an effective amount of a differentiation-inducing agent is an amount sufficient to cause a precursor cell to differentiate in in vitro culture into a cell of a tissue at predetermined site of treatment. It is understood that an "effective amount" can vary depending on various conditions including, but not limited to the stage of differentiation of the precursor cell, the origin of the precursor cell, and the culture conditions.

The terms "inhomogeneous", "inhomogeneity", "heterogeneous", "heterogeneity", and grammatical variations thereof, are meant to refer to a fiber, substrate, textile, and/or fabric as disclosed herein that does not have a homogeneous composition along a given length or in a given volumetric section. In some embodiments, an inhomogeneous tissue engineering construct as disclosed herein comprises a composite material, such as a composite comprising a three dimensional woven fiber substrate, textile, and/or fabric as disclosed herein, cells that can develop tissues that substantially provide the function of periosteum, cartilage, other tissues, or combinations thereof, and a matrix that supports the cells. In some embodiments, an inhomogeneous substrate as disclosed herein can comprise one or more component systems that vary in their properties according to a predetermined profile, such as a profile associated with the tissue and/or other location in a subject where the substrate will be implanted. Thus, it is an aspect of the terms "inhomogeneous", "inhomogeneity", "heterogeneous", "heterogeneity", and grammatical variations thereof to encompass the control of individual materials and properties in the substrate.

The terms "non-linear", "non-linearity", and grammatical variations thereof, refer to a characteristic provided by a fiber substrate, textile, and/or fabric as disclosed herein such that the fiber substrate, textile, and/or fabric can vary in response to a strain. Fiber substrate, textile, and/or fabric disclosed herein can provide stress/stain profiles that mimic that observed in a target or region of interest.

The terms "resin", "matrix", or "gel" are used in the art-recognized sense and refer to any natural or synthetic solid, liquid, and/or colloidal material that has characteristics suitable for use in accordance with the presently disclosed subject matter. Representative "resin", "matrix", or "gel" materials thus comprise biocompatible materials. In some embodiments, the "resin", "matrix", or "gel" can occupy the pore space of a fiber scaffold as disclosed herein.

The terms "viscoelastic", "viscoelasticity", and grammatical variations thereof, are meant to refer to a characteristic provided by a fiber substrate, textile, and/or fabric as disclosed herein that can vary with a time and/or rate of loading.

Embodiments describe herein relate to engineered materials whose structure is based on structural protein components of extracellular matrix of biological materials of, for example, animals and plants, as well as methods of forming the engineered materials. The engineered materials can replicate or mimic biological material's or nature's intrinsic architecture of structural molecules, such as proteins, by translation of nature's protein weaving algorithms to weave scaled-up, multidimensional fabric or textile architectures emulating natural fabric organization. The methods and engineered materials described herein can provide mechanically functional textiles, including engineered tissue fabrics and tissue implants, and materials for transport and safety industries.

Figure 1:
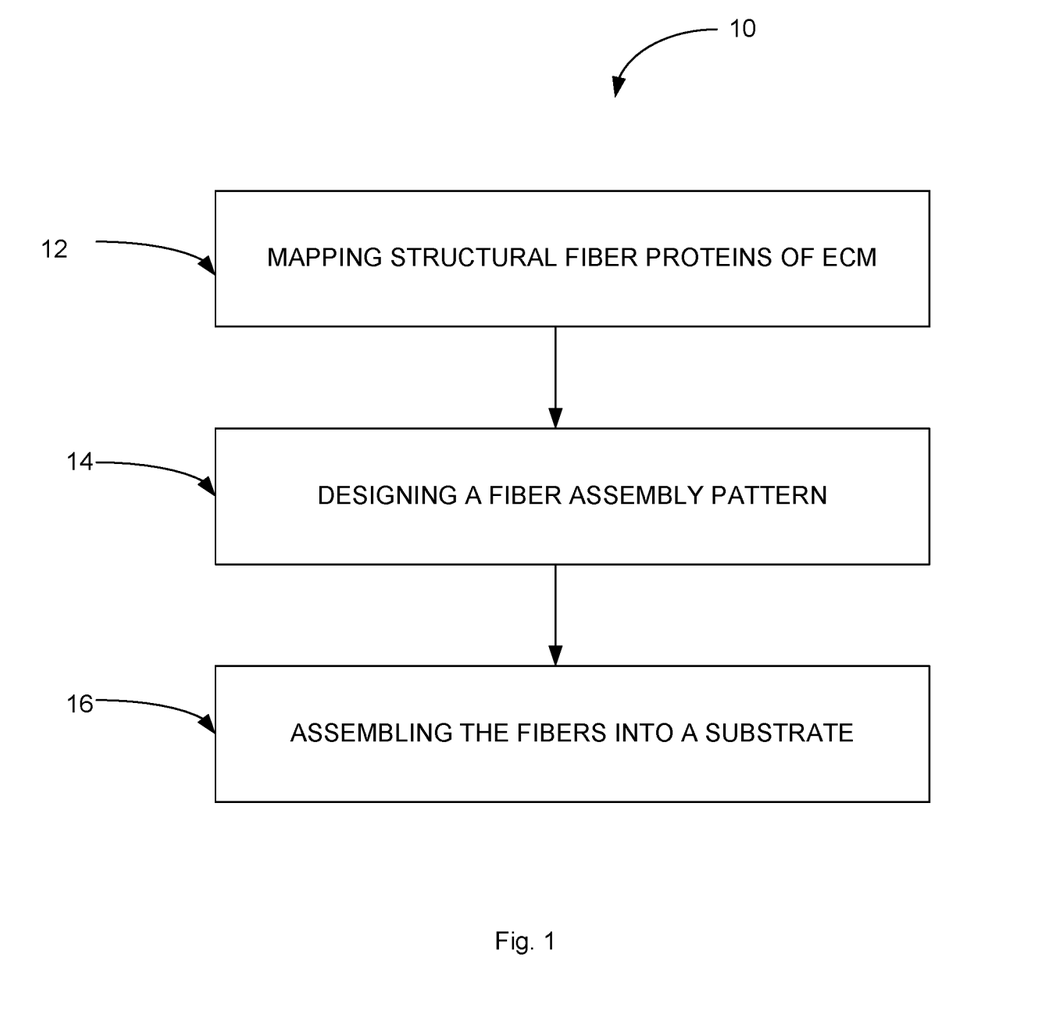
FIG. 1 is a flow chart showing the method of constructing tissue.

FIG. 1 is a flow diagram illustrating a method 10 of forming a substrate or textile of an engineered material, such as a biomedical material, tissue implant, or mechanically functional textile. In the method 10, at step 12 a three dimensional spatial distribution of at least one structural molecule of extracellular matrix of biological material of interest is mapped. In some embodiments, the structural molecule can include a structural protein fiber such as collagen fibers, elastin fibers, fibronectin fibers, and laminin fibers. In some examples, the at least one structural protein fiber can include collagen fibers and elastin fibers (and/or natural or synthesized analogs thereof) of the extracellular matrix of the biological material.

The biological material can include any biological material that comprises an extracellular matrix of structural protein fibers including tissue of a plant or animal. The tissue can include, for example, at least one or periosteum, pericardium, perimycium, or tissue bounding an organ or tissue compartment (e.g., tree bark).

Regions of interest (ROI) of the biological material can be imaged and mapped to highlight collagen and elastin fibers in context of tissue compartments (bone, muscle, vasculature) and their respective microscopic structures along the major and minor axes. These axes, calculated using an automated software, can serve, for example, as objective indicators of tissue regions most and least able to resist bending forces in the axial plane. For each ROI, a tiled image of the transverse (xy) plane, followed by a z-stack of one tile within the region, can be captured to map in 3D space the composition and distribution of the collagen and elastin fibers as well as their higher order architectures.

In some embodiments, the three dimensional spatial distribution of the structural protein fibers (e.g., collagen fibers and elastin fiber) can be mapped or imaged using multimodal imaging of section or transverse section of the biological material. For example, the three dimensional spatial distribution of the collagen fibers and the elastin fibers can be mapped using, respectively, second harmonic imaging microscopy and two photon excitation imaging microscopy of transverse section of ROI of the biological material.

Second harmonic imaging microscopy (SHIM) can be used to capture high-resolution, high-content, 3D representations of fibrillar collagen in live and ex vivo tissue without the need for exogenous labeling. In SHIM, a frequency doubling of the incident light occurs in repetitive and non-centrosymmetric molecular structures.

By way of example, biological specimens can be imaged using a Leica SP5 II inverted microscope equipped with a Spectra Physics MaiTai HP DeepSea titanium sapphire multiphoton laser tuned to 830 nm (~100 fs pulse), a xyz high precision multipoint positioning stage and a 63× 1.3NA glycerol objective. The forward propagated second harmonic collagen signal can then be collected in the transmitted Non-Descanned-Detector using a 390-440 nm bandpass filter.

The two-photon imaging of elastin can be performed by excitation of the biological specimen at 830 nm and following by collection using a photo-multiplier tube (PMT) with a 435-495 nm emission filter. This filter can be used to segment away autofluorescence.

The images can then collated to create to create scaled up three dimensional maps or models, which accurately represent the composition and spatial architecture of the image sequences and the extracellular matrix, biological material, and/or tissue itself. The three dimensional maps can include not only the spatial distribution of the collagen fibers and elastin fibers but also other features or structures of the extracellular matrix including vasculature that extends through the matrix.

Following mapping of the three dimensional spatial distribution of at least one structural molecule, e.g., collagen fiber and elastin fiber, of the extracellular matrix, at step 14, a fiber assembly pattern can be designed based on an intrinsic pattern of the at least one structural protein fiber of the extracellular matrix of the biological material. In some embodiments, the fiber assembly pattern can include a weaving algorithm or weaving motif based on the intrinsic pattern of the mapped three dimensional spatial distribution of the collagen fibers and the elastin fibers as well as other structural features of the extracellular matrix, such as vasculature. In some instances, the intrinsic pattern of the collagen fibers and the elastin fibers can be used to design or generate a custom-configured jacquard weaving algorithm (ArahWeave, arahne CAD/CAM for weaving) for weaving of physical prototypes (AVL Looms, Inc.).

Following design of the fiber assembly pattern, at step 16, fibers are woven in a weave pattern and/or fiber orientation based on the fiber assembly pattern or weaving algorithm to form the substrate, textile or fabric of the engineered material. The fibers woven using the weaving algorithm can be monofilament, multifilament, or a combination thereof, and can be of any shape or cross-section including, but not limited to bracket-shaped (i.e., D, polygonal, square, I-beam, inverted T shaped, or other suitable shape or cross-section. The cross-section can vary along the length of fiber. Fibers can also be hollow to serve as a carrier for bioactive agents (e.g., antibiotics, growth factors, etc.), cells, and/or other materials as described herein. In some embodiments, the fibers can serve as a degradable or nondegradable carriers to deliver a specific sequence of growth factors, antibiotics, or cytokines, etc., embedded within the fiber material, attached to the fiber surface, or carried within a hollow fiber. The fibers can each comprise a biocompatible material, and the biocompatible material can comprise an absorbable material, a non-absorbable material, or combinations thereof.

Fiber diameters can be of any suitable length in accordance with characteristics engineered material's use or function. Representative size ranges include a diameter of about 1 micron, about 5 microns, about 10 microns about 20 microns, about 40 microns, about 60 microns, about 80 microns, about 100 microns, about 120 microns, about 140 microns, about 160 microns, about 180 microns, about 200 microns, about 220 microns, about 240 microns, about 260 microns, about 280 microns, about 300 microns, about 320 microns, about 340 microns, about 360 microns, about 380 microns, about 400 microns, about 450 microns or about 500 microns (including intermediate lengths). In various embodiments, the diameter of the fibers can be less than about 1 micron or greater than about 500 microns. Additionally, nanofibers fibers with diameters in the nanometer range (1-1000 nanometers) are envisioned for certain embodiments. Additionally, large fibers with diameters up to 3.5 cm are envisioned for certain embodiments.

In other embodiments, the fibers or subset of fibers, can contain one or more bioactive or therapeutic agents such that the concentration of the bioactive or therapeutic agent or agents varies along the longitudinal axis of the fibers or subset of fibers. The concentration of the active agent or agents can vary linearly, exponentially or in any desired fashion, as a function of distance along the longitudinal axis of a fiber. The variation can be monodirectional; that is, the content of one or more therapeutic agents can decrease from the first end of the fibers or subset of the fibers to the second end of the fibers or subset of the fibers. The content can also vary in a bidirectional fashion; that is, the content of the therapeutic agent or agents can increase from the first ends of the fibers or subset of the fibers to a maximum and then decrease towards the second ends of the fibers or subset of the fibers.

Thus, in some embodiments, the fibers serve as a degradable or nondegradable carrier to deliver one or more specific sequences of growth factors, antibiotics, cytokines, etc. that are embedded within the fiber matter, attached to the fiber surface, or carried within a hollow fiber.

In some embodiments, the fibers woven to form the substrate, textile, or fabric can be prepared in a hydrated form or it can be dried or lyophilized into a substantially anhydrous form.

In other embodiments, the fibers can be biodegradable over time, such that it will be absorbed into a subject if implanted in a subject. Woven fiber substrates, which are biodegradable, can be formed from monomers, such as glycolic acid, lactic acid, propyl fumarate, caprolactone, hyaluronan, hyaluronic acid, and the like. Other fiber substrates can include proteins, polysaccharides, polyhydroxy acids, polyorthoesthers, polyanhydrides, polyphosazenes, or synthetic polymers (particularly biodegradable polymers). In some embodiments, polymers for forming the fiber substrates can include more than one monomer (e.g., combinations of the indicated monomers). Further, the fiber substrate can include hormones, such as growth factors, cytokines, and morphogens (e.g., retinoic acid, arachidonic acid, etc.), desired extracellular matrix molecules (e.g., fibronectin, laminin, collagen, etc.), or other materials (e.g., DNA, viruses, other cell types, etc.) as desired.

Polymers used to form the fibers can include single polymer, co-polymer or a blend of polymers of poly(L-lactic acid), poly(DL-lactic acid), polycaprolactone, poly(glycolic acid) or polyanhydride. Naturally occurring polymers can also be used such as reconstituted or natural collagens or silks. Those of skill in the art will understand that these polymers are just examples of a class of biodegradable polymers that can be used in the presently disclosed subject matter. Further biodegradable polymers include polyanhydrides, polyorthoesters, and poly(amino acids).

Examples of natural polymers that can be used for the fibers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers can include, for example, proteins, such as albumin.

Examples of semi-synthetic polymers that can be used to form the fibers include carboxymethylcellulose, hydroxymethylcellulose, hydroxypropylmethylcellulose, methylcellulose, and methoxycellulose. Exemplary synthetic polymers include polyphosphazenes, polyethylenes (such as, for example, polyethylene glycol (including the class of compounds referred to as PLURONICS, commercially available from BASF, Parsippany, N.J., U.S.A.), polyoxyethylene, and polyethylene terephthlate), polypropylenes (such as, for example, polypropylene glycol), polyurethanes, polyvinyl alcohol (PVA), polyvinyl chloride and polyvinylpyrrolidone, polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof.

In some embodiments, the fibers can be assembled into a three dimensional fiber substrate, textile, or fabric using a 3-D computer controlled weaving loom, such as a jacquard loom, specifically constructed to produce precise structures from fine diameter fibers. The weaving pattern of the woven substrate, textile, or fabric is defined by the fiber assembly pattern or weaving algorithm designed from the intrinsic pattern of the mapped structural molecules, e.g., structural protein fibers, of the extracellular matrix of the biologic material.

The weaving pattern and/or weaving algorithm can also use or incorporate spatial and temporal patterns of (in-)elasticity to create dynamic pressures, such as described in WO2015/021503. The method of forming a substrate having at least one region of temporally-controlled elasticity may include a step of weaving threads having varying composition and/or elasticity along their length into the substrate.

A computer controlled weaving machine can produce true 3-D shapes by placing fibers axially (x-warp direction), transversely (y-weft, or filling direction), and vertically (z-thickness direction). Multiple layers of warp yarns are separated from each other at distances that allow the insertion of the weft layers between them. Two layers of Z-yarns, which are normally arranged in the warp direction, are moved (after the weft insertion) up and down, in directions opposite to the other. This action is followed by the "beat-up", or packing of the weft into the scaffold, and locks the two planar fibers (the warp and weft) together into a uniform configuration. Change of yarn densities can be achieved for warp by altering the reed density and warp arrangement and for weft by varying the computer program controlling the take-up speed of a stepper motor.

An advantage of the presently disclosed weaving technique is that each fiber can be selected individually and woven into a substrate, textile, and/or fabric. Using this method of assembly, customized structures can be easily created by selectively placing different constituent fibers (e.g., fibers of various material composition, size, and/or coating/treatment) throughout the substrate, textile, and/or fabric. In this manner, physical and mechanical properties of the substrate, textile, and/or fabric can be controlled (i.e., pore sizes can be selected, directional properties can be varied, and discreet layers can be formed). Using this technique, the inhomogeneity and anisotropy of various tissues can be reproduced by constructing a substrate, textile, and/or fabric that mimics the normal stratified structural network using a single, integral substrate, textile, and/or fabric.

In some embodiments, the fibers can be provided as threads that are oriented in space relative to each other during the assembly step. The assembly step includes can including orienting threads having different elasticity along their length according to a predetermined algorithm.

In other embodiments, yarns of the fibers after assembly can be set via any of a number of art-recognized techniques, including but not limited to ultrasonication, a resin, infrared irradiation, heat, or any combination thereof. Setting of the yarn systems within the scaffold in this manner provides cuttability and suturability. Sterilization can be performed by routine methods including, but not limited to autoclaving, radiation treatment, hydrogen peroxide treatment, ethylene oxide treatment, and the like.

Representative methods for making three-dimensional textile structures are also disclosed in U.S. Pat. Nos. 5,465,760 and 5,085,252, the contents of each of which are incorporated herein by reference in their entireties. The following patent publications are also incorporated herein by reference in their entireties: PCT International Patent Application Publication WO 01/38662 (published May 31, 2001); PCT International Patent Application Publication WO 02/07961 (published Jan. 31, 2002); U.S. Patent Application Publication 2003/0003135 (published Jan. 2, 2003), and PCT International Patent Application Serial No. PCT/US06/14437, filed Apr. 18, 2006.

In some embodiments, the woven fiber substrate, textile, and/or fabric so formed can be used to generate engineered tissue implant or mechanically functional textiles, which can be used to treat and/or repair tissue defects, such as bone defects or soft tissue defects. The woven fiber substrate, textile, and/or fabric can be used in its native form, as a composite material in combination with other materials, as an acellular (non-viable) matrix, or combined with at least one cell and/or at least one bioactive agents (e.g., growth factors) for use in repair, regeneration, and/or replacement of diseased or traumatized tissue and/or tissue engineering applications. An advantage of the presently disclosed subject matter is the ability to produce biomaterial scaffolds and composite matrices that have precisely defined mechanical properties that can be inhomogeneous (vary with site), anisotropic (vary with direction), nonlinear (vary with strain), and/or viscoelastic (vary with time or rate of loading) and that mimic native or natural tissue to be treated and/or repaired. By combining a fiber-based scaffold with a biocompatible resin or matrix, another advantage of the composite matrix is that the microenvironment of embedded cells can be controlled to promote appropriate cell growth and/or activity while providing for the prescribed mechanical properties.

The at least one bioactive agent provided in the fiber scaffold can include polynucleotides and/or polypeptides encoding or comprising, for example, transcription factors, differentiation factors, growth factors, and combinations thereof. The at least one bioactive agent can also include any agent capable of promoting tissue formation (e.g., bone and/or cartilage), destruction, and/or targeting a specific disease state (e.g., cancer). Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

The at least one cell provided in the fiber scaffold can include any progenitor cell, such as a totipotent stem cell, a pluripotent stem cell, or a multipotent stem cell, as well as any of their lineage descendant cells, including more differentiated cells (described above). The cells can include autologous cells; however, it will be appreciated that xenogeneic, allogeneic, or syngeneic cells may also be used. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to introduction into the woven fiber substrate, textile, and/or fabric. For example, autologous cells can be expanded in this manner if a sufficient number of viable cells cannot be harvested from the host. Alternatively or additionally, the cells may be pieces of tissue, including tissue that has some internal structure. The cells may be primary tissue explants and preparations thereof, cell lines (including transformed cells), or host cells.

In some embodiments, the woven fiber substrate, textile, and/or fabric can be mixed or embedded with cells and crosslinked to form a hydrogel matrix containing the cells before or after implantation into the body. The woven fiber substrate, textile, and/or fabric functions to provide a template for the integrated growth and differentiation of the desired tissue. In some embodiments, a polymer forms the hydrogel within the body upon contact with a crosslinking agent. A hydrogel is defined as a substance formed when an organic polymer (natural or synthetic) is crosslinked via covalent, ionic or hydrogen bonds to create a three-dimensional open, woven fiber substrate, textile, and/or fabric, which entraps water molecules to form a gel. Naturally occurring and synthetic hydrogel forming polymers, polymer mixtures and copolymers can be utilized as hydrogel precursors. See, for example, U.S. Pat. No. 5,709,854 and WO 94/25080.

Hydrogels can be classified into two broad categories: reversible or physical and irreversible or chemical. The networks in physical gels are held together by molecular entanglements and/or secondary forces including ionic, hydrogen bonding or hydrophobic forces. Physical hydrogels are characterized by significant changes in the rheological properties as a function of temperature, ionic concentration, and dilution. Chemical gels, also called permanent gels, are characterized by chemically crosslinked networks. When crosslinked, these gels reach an equilibrium swelling level in aqueous solutions which depends mainly on the crosslink density.

The preparation of hydrogels can be achieved by a variety of methods well known to those of ordinary skill in the art. Physical gels can be formed by: heating or cooling certain polymer solutions (cool agarose, for example), using freeze-thaw cycles to form polymer microcrystals, reducing the solution pH to form a hydrogen-bonded gel between two different polymers in the same aqueous solution, mixing solutions of a polyanion and a polycation to form a complex coacervate gel, gelling a polyelectrolyte solution with a multivalent ion of opposite charge, reticulation of linear polymers, grafting of synthetic polymers onto naturally occurring macromolecules, and chelation of polycations (Hoffman (2000) Advanced Drug Delivery Reviews, 43:3-12). Chemical gels can be created by crosslinking polymers in the solid state or in solution with radiation, chemical crosslinkers like glutaraldehyde, or multifunctional reactive compounds. They can also be made by copolymerizing a monomer and a crosslinker in solution, copolymerizing a monomer and a multifunctional macromer, polymerizing a monomer within a different solid polymer to form an IPN gel, or chemically converting a hydrophobic polymer to a hydrogel (Hennick and van Nostrum (2002) Advanced Drug Delivery Reviews, 54:13-26).

An exemplary method for combining the woven fiber substrate, textile, and/or fabric with a gel matrix is via the utilization of a vacuum-assisted molding process. Particularly, the technique utilizes vacuum pressure to draw the gel while still in its liquid form into the woven fiber substrate, textile, and/or fabric, effectively filling the pore spaces and encapsulating the fibers. Once the gel has completely infused the scaffold, it is solidified by an appropriate crosslinking method to form the composite construct. In some embodiments, cells and/or growth promoting materials are seeded into the woven fiber substrate, textile, and/or fabric by mixing them into a liquid gel prior to infusion into a woven fiber substrate, textile, and/or fabric.

Thus, the woven fiber substrate, textile, and/or fabric, which in some embodiments are 3-D orthogonally woven fiber performs, can be infiltrated with a cell-seeded or acellular gel material to form a composite construct or bioartificial implant. In some embodiments, the cells can be primary cells and/or undifferentiated progenitor cells. The gel biomaterial can be one of many different types of crosslinkable, photocrosslinkable, temperature sensitive, and/or other gel that can sustain cell growth and provide mechanical function to the scaffold. Possible gels include fibrin, alginate, agarose, elastin, chitosan, collagen, etc.

In some embodiments, to form the fiber scaffold, the cells are introduced onto the woven fiber substrate, textile, and/or fabric such that they permeate into the interstitial spaces therein. For example, the matrix can be soaked in a solution or suspension containing the cells, or they can be infused or injected into the matrix. In some embodiments, a hydrogel is formed by crosslinking a suspension comprising the fiber and the inventive cells dispersed therein. This particular method of formation permits the cells to be dispersed throughout the woven fiber substrate, textile, and/or fabric, facilitating more even permeation of the woven fiber substrate, textile, and/or fabric with the cells. As would be readily apparent to one of ordinary skill in the art, the composition can include mature cells of a desired phenotype or precursors thereof, particularly to potentate the induction of the inventive stem cells to differential appropriately within the woven fiber substrate, textile, and/or fabric (e.g., as an effect of co-culturing such cells within the woven fiber substrate, textile, and/or fabric).

In some embodiments, the woven fiber substrate, textile, and/or fabric can be coated on one or more surfaces, before or after consolidation with a gel and/or cells, with a material to improve the mechanical, tribological, or biological properties of the composite. Such a coating material can be resorbable or non-resorbable and can be applied by dip-coating, spray-coating, electrospinning, plasma spray coating, and/or other coating techniques. The material can be a single or multiple layers or films. The material can also comprise randomly aligned or ordered arrays of fibers. In some embodiments, the coating can comprise electrospun nanofibers. The coating material can be selected from the group including, but not limited to polypropylene, polyester, polytetrafluoroethylene (PTFE), expanded PTFE (ePTFE), polyethylene, polyurethane, polyamide, nylon, polyetheretherketone (PEEK), polysulfone, a cellulosic, fiberglass, an acrylic, tantalum, polyvinyl alcohol, carbon, ceramic, a metal, polyglycolic acid (PGA), polylactic acid (PLA), polyglycolide-lactide, polycaprolactone, polyethylene glycol) (PEG), polydioxanone, polyoxalate, a polyanhydride, a poly(phosphoester), catgut suture, collagen, silk, chitin, chitosan, hydroxyapatite, bioabsorbable calcium phosphate, hyaluronic acid, elastin, lubricin, and combinations thereof.

In some embodiments a smooth surface coat on the woven fiber substrate, textile, and/or fabric is thus provided if needed. In some embodiments, the surface coat can increase durability and/or reduce friction of and/or at the surface.

In some embodiments, the woven fiber substrate, textile, and/or fabric can be employed in any suitable manner to facilitate the growth and generation of the desired tissue types or structures. For example, the woven fiber substrate, textile, and/or fabric can be constructed using three-dimensional or stereotactic modeling techniques. Thus, for example, a layer or domain within the woven fiber substrate, textile, and/or fabric can be populated by cells primed for one type of cellular differentiation, and another layer or domain within the woven fiber substrate, textile, and/or fabric can be populated with cells primed for a different type of cellular differentiation. As disclosed herein and as would be readily apparent to one of skill in the art, to direct the growth and differentiation of the desired structure, in some embodiments, the woven fiber substrate, textile, and/or fabric can be cultured ex vivo in a bioreactor or incubator, as appropriate. In some embodiments, the structure is implanted within the subject directly at the site in which it is desired to grow the tissue or structure. In further embodiments, the woven fiber substrate, textile, and/or fabric can be grafted on a host (e.g., an animal such as a pig, baboon, etc.), where it can be grown and matured until ready for use, wherein the mature structure is excised from the host and implanted into the subject.

Thus, provided in some embodiments is a novel woven fiber substrate, textile, and/or fabric for the growth of tissues/organs both in vitro and in vivo. In particular embodiments, provided is a biodegradable woven fiber substrate, textile, and/or fabric of made with collagen, elastin, or natural and/or synthetic analogs thereof and/or \composite material to be placed in either a bioreactor or a directly into a living bio-organism for the purpose of replacing a damaged and/or missing tissue, wherein the engineered material comprises mechanical structures for stimulating cells.

Example

Figure 2A:
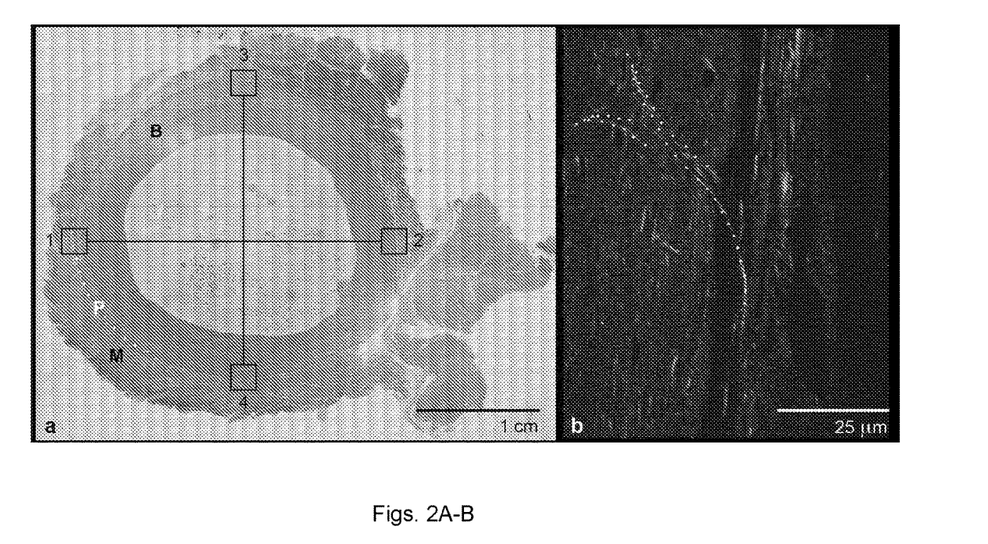
Figure 2C:
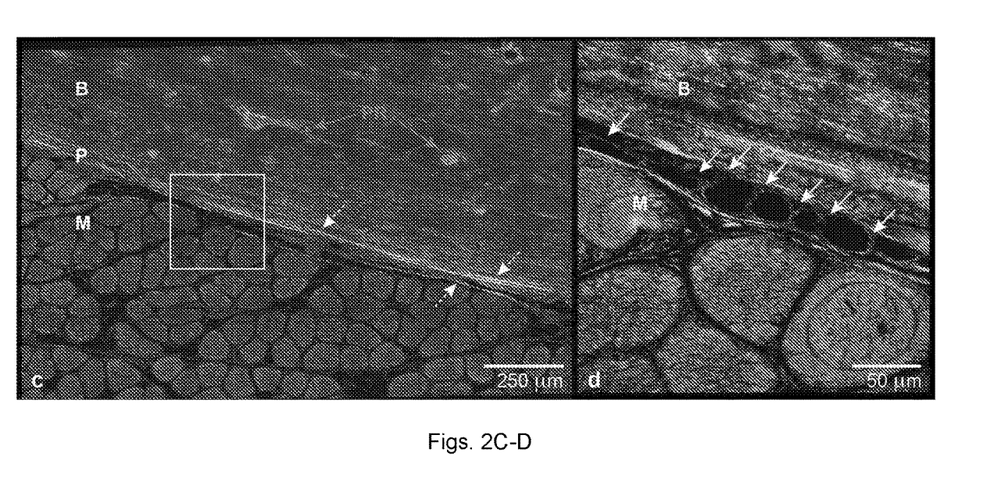
Figure 2E:
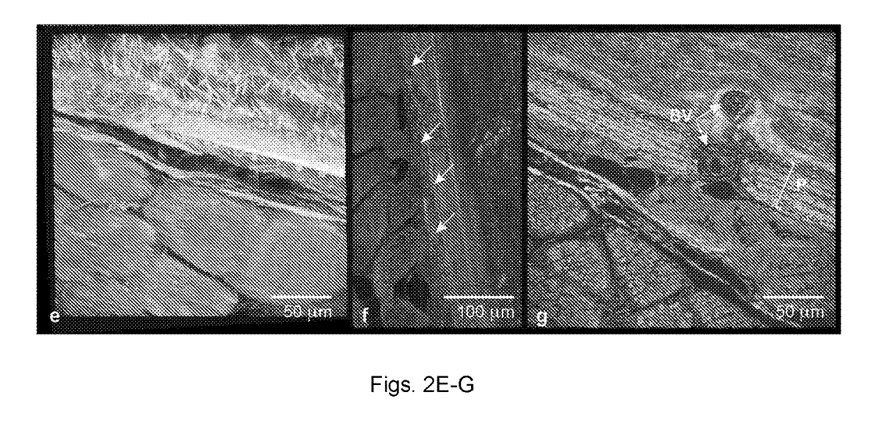
Figure 3A:
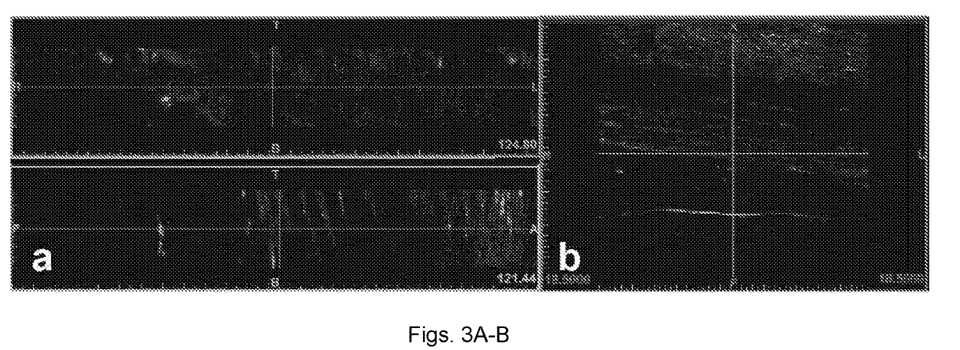
Figure 3C:
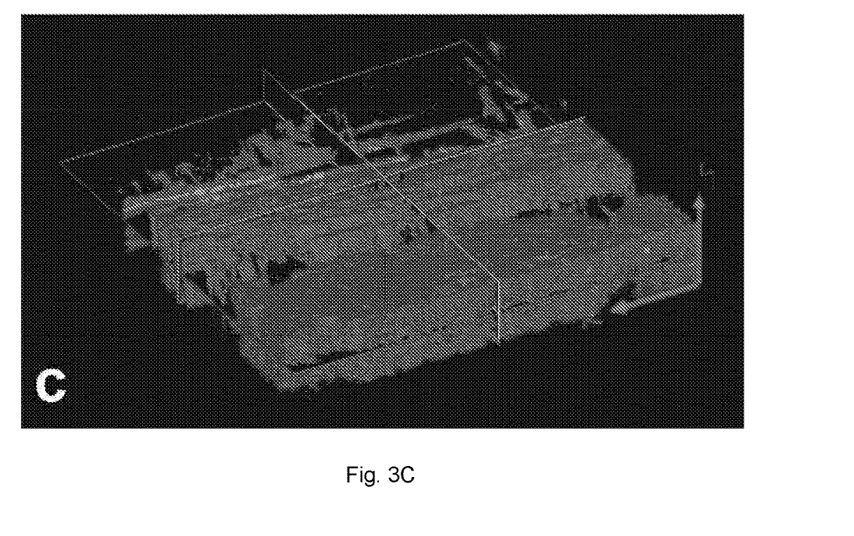
Figure 3D:
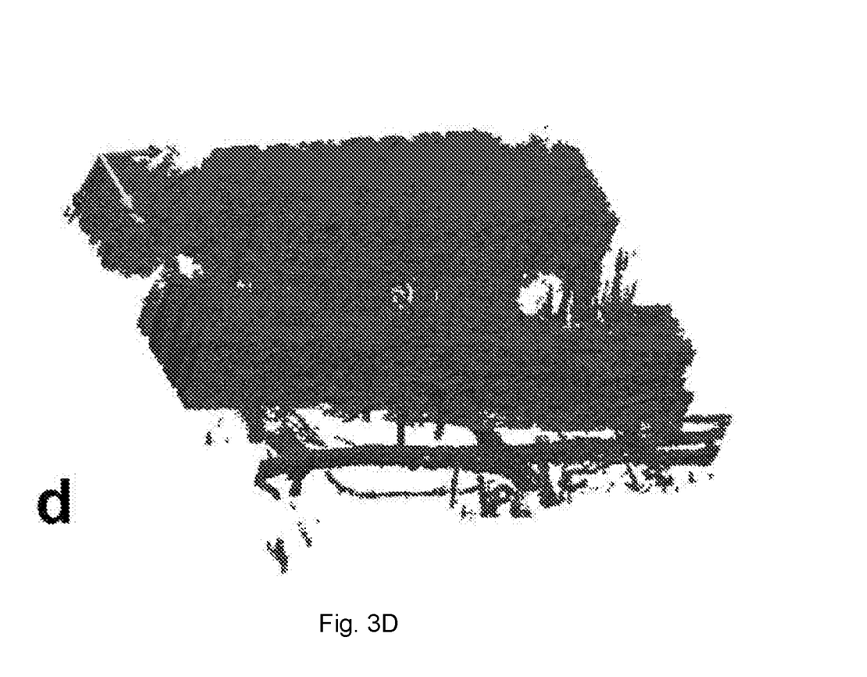
Figure 3E:
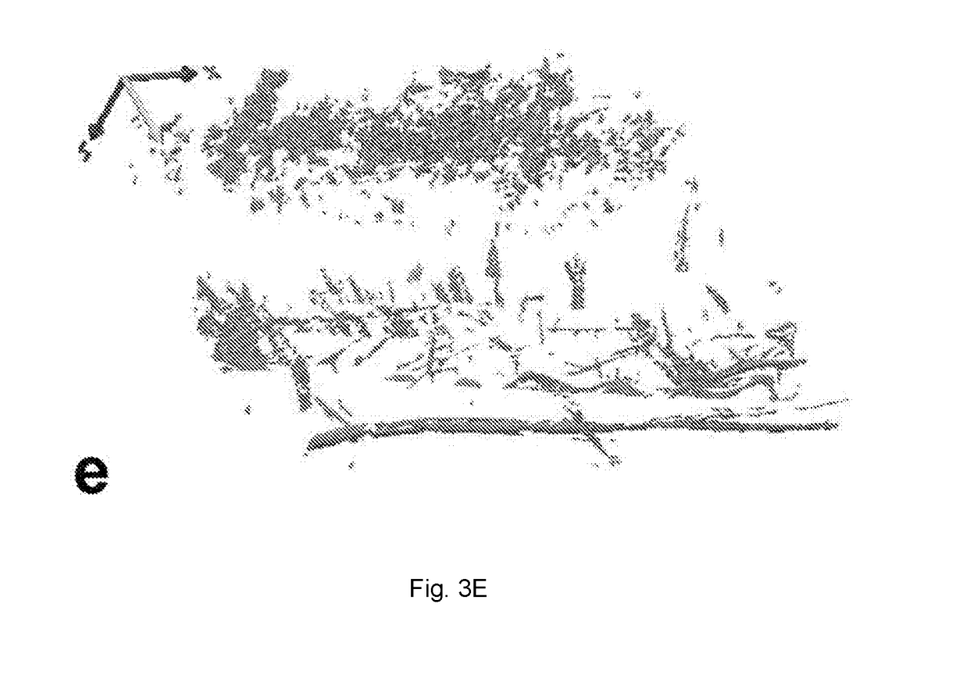
Figure 3F:
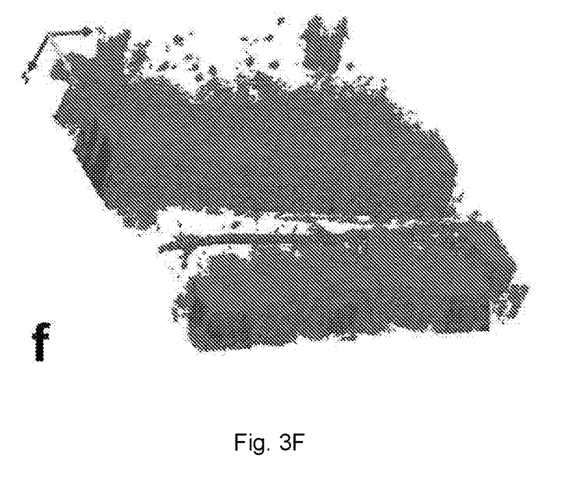
Figure 3G:
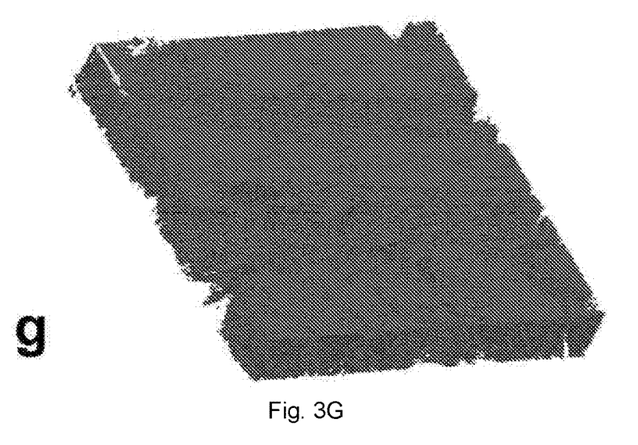
Figure 3H:
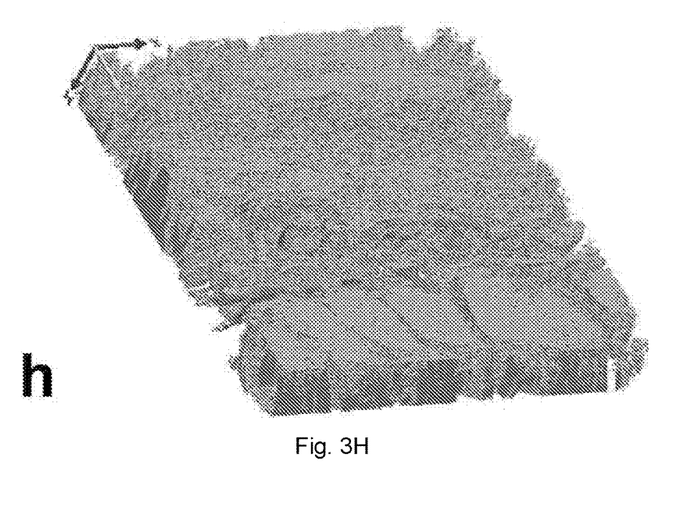
Figure 3I:
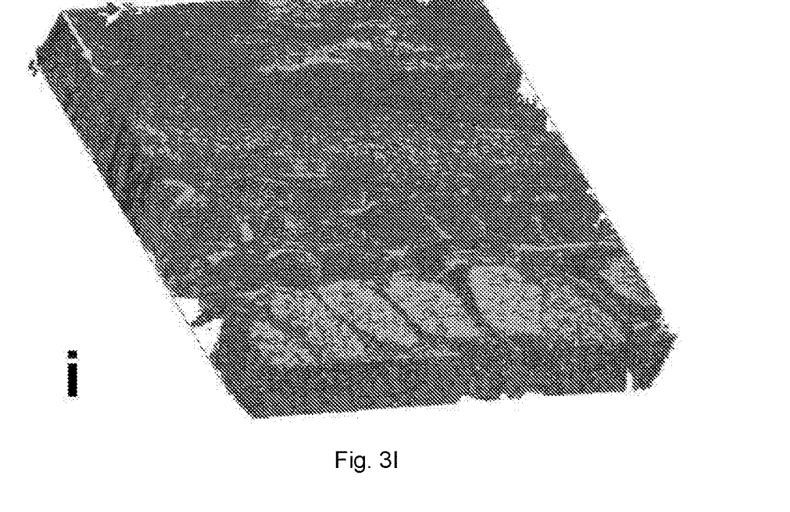
Figure 4A:
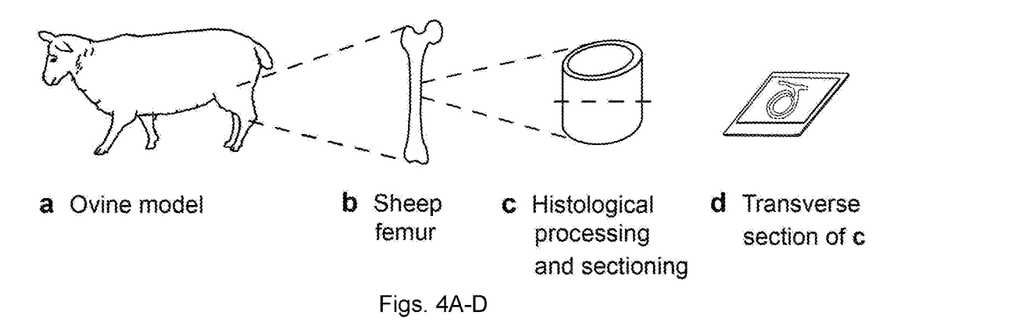

In this example, we show the inherent functional capacity of periosteum by investigating its architecture, i.e. multiscale 3D distribution of its collagen and elastin fibers, via second harmonic generation and two-photon excitation microscopy (FIG. 2). We then tested the feasibility of rendering these natural tissue weaves using computer-aided design software (FIG. 3) and scaling up nature's patterns to weave periosteum-inspired, multidimensional fabrics with a jacquard loom (FIG. 4).

Second Harmonic Imaging Microscopy (SHIM) of Collagen and Two Photon Excitation Microscopy (TPEM) of Elastin SHIM has emerged as a robust tool to capture high-resolution, high-content, 3D representations of fibrillar collagen in live and ex vivo tissue without the need for exogenous labeling. In SHIM, a frequency doubling of the incident light occurs in repetitive and non-centrosymmetric molecular structures. The resulting coherently propagated waveform is not accompanied by a loss of energy nor is subject to photobleaching, making it an ideal technique to examine and quantify endogenous collagen functional textiles.

Here, we first validate our combined SHIM-TPEM protocol on periosteum from sheep specimens prepared using standard protocols for undecalcified histology. Transverse sections were prepared from the ovine femoral diaphysis with intact surrounding musculature and vasculature stained in vivo using procion red per previous protocols. Regions of interest (ROI) were imaged to highlight collagen and elastin fibers in context of tissue compartments (bone, muscle, vasculature) and their respective microscopic structures along the major and minor axes of the diaphyseal shaft; these axes, calculated using an automated software, serve as objective indicators of tissue regions most and least able to resist bending forces in the axial plane. For each ROI, a tiled image of the transverse (xy) plane, followed by a z-stack of one tile within the region, was captured to map in 3D space the composition and distribution of the collagen and elastin fibers as well as their higher order architectures.

The resulting merged tiled images demonstrate the high collagen content of bone and high elastin content of muscle (FIG. 2). The thickness and composition of periosteum varies depending on proximity to nearby tissue compartments and structures such as muscle and vasculature. Where muscle or their fasciae adjoin to periosteum, the periosteum thickens, particularly in the posterior aspect. The periosteum and its neighboring muscle fasciae exhibit a varying composition and architecture of both collagen and elastin fibers. In some areas, fibers with a strong SHG signal, attributed to collagen, run along the bone's circumference, though not spanning the entire ROI. These fibers represent components of periosteum's fibrous layer, and their anisotropic arrangement likely underpins periosteum's anisotropic mechanical reinforcement function and direction-dependent permeability.

In other areas, collagen fibers insert at a slight angle directly into bone, indicative of Sharpey's fiber structure and intrinsic function transducing force between muscle and bone (FIG. 2). The Sharpey's collagen fiber bundles are thicker and emit a stronger signal than the collagen fibers within the periosteum sleeve composite. The thickness of the reflected fiber correlates to its contrast intensity, which varies as a function of the angle between the fiber and the laser beam. Thus, for the first time to our knowledge, we were able to track in 3D space (in an approximately 40 μm thick z-stack) the angled collagen fibers making up single Sharpey's fibers as they exit the periosteum and anchor into bone (FIG. 2B). Similarly, we also were able for the first time to visualize the interaction of the periosteum's collagen fibers with neighboring muscle fascia and perimysium. Particularly in regions where muscle fascicles are in close association with the periosteum, collagen fibrils can be seen linking the periosteum to the perimysium, another indicator of direct force transfer (FIG. 2F). Though collagen is much less evident in the muscle per se, SHIM enables visualization of thin collagen fibers in the fasciae bordering muscle groups, perhaps providing mechanical support and stability during muscle distension. Based on these observations, we envision the muscle fascia as a continuous collagen comprised bounding layer spanning superficial and deep muscle layers to the periosteum and finally, bone. In sum, the collagen fibers themselves exhibit different structures in different tissues, with loose and wavy collagen strands in muscle regions, to dense and straight bundles closer to the bone, and higher order architectures such as Sharpey's fibers evident between tissue compartments. Of particular note, collagen and its analogs impart tissues with toughness, which maximizes the material's capacity to absorb energy prior to failure. In contrast, elastin and its analogs impart tissues with elasticity, which maximizes the material's capacity to deform without causing permanent deformation to the material.

Imaged in the transverse section of the long bone sample, the TPEM visualized elastin components of the periosteum resemble tree bark. The elastin signal is also detected in muscle tissue structures, providing architectural information for fibers within muscle fascia, perimysium and blood vessels. With regards to muscle, distinct muscle groups can be seen adhering directly to the periosteum in some regions (FIG. 2F) with other areas connected via elastin coils resembling springs (FIG. 2D). In some ROIs multiple such coils formed a loosely woven webbed structure. These spatially varying features likely reflect the local mechanical environment of the tissue, e.g. elastin springs would maximize flexibility while providing elastic dampers during maximal muscle distension and spring back. Blood vessels, identified through the strong elastin signal of the vessel walls containing procion red filled channels, present abundantly in association with the periosteum (FIG. 2G). Some blood vessels transect the periosteal layer to form the Volkmann canals which insert into cortical bone and connect with the axially aligned Haversian channels. This multifunctional physiological tapestry comprises the fibrous weave of elastin and its higher order architecture into tissue fabric, bridging structures and vascular channels, underscoring the emergent structures which underlie the smart mechanical and permeability properties of the periosteum.

Imaging the periosteum using SHIM and TPEM enables high resolution mapping of elastin and collagen fibers and their higher order architectures in context of surrounding tissue compartments. As a next step in our bottom-up approach we used the z-stacks from our novel microscopy protocol to create scaled up 3D models which accurately represent the composition and spatial architecture of the image sequences and the tissue itself (FIG. 3). To achieve this, each channel in the z-stack was imported separately as an image sequence into Mimics® for 3D rendering (Materialise, MIS v18.0 Beta) and then masked according to its signal intensity. The masks were converted to STL files and combined to create a composite 3D model comprising collagen, elastin and vascular components (FIG. 4). This model then served as a pattern template for a custom-configured jacquard weaving algorithm (ArahWeave, arahne CAD/CAM for weaving) and for weaving of physical, scaled up prototypes (AVL Looms, Inc.). Taken together, this approach demonstrates the feasibility of using SHIM in combination with TPEM to develop and prototype structurally relevant, scaled-up woven prototypes mimicking the sophisticated, complex and composite tissue fabric of periosteum.

The acquisition of high-resolution, architecturally accurate 3D models enables rapid prototyping using computer-controlled weaving and/or other rapid prototyping modalities while limiting the inherent stochasticity of natural systems as well as their virtual models. Other contemporary rapid prototyping techniques have been applied to manufacture tissue engineering scaffolds including electrospinning of nanoscaffolds, 3D organ printing and integrative weaving of porous cartilage scaffolds. Developments in electrospun nanofiber scaffolds enable the creation and manipulation of scaffolds at the cellular length scale, although this manufacturing process is not yet amenable to customization of the architecture, geometry and mechanical attributes needed to mimic the composite and sophisticated material properties of the periosteum or other similarly complex tissues. 3D printing offers distinct advantages with regard to flexibility in customizing geometries but is not yet effective for prototyping pieces with seamless mechanical gradients or parts that can withstand dynamic tension and bending. To date, integrative weaving has not yet captured the detailed fiber arrangement of biological tissues. Hence, to our knowledge, this study is the first of its kind, where natural woven architectures are mapped and replicated in scaled-up models to develop novel advanced materials and functional textiles. The only other potential way to replicate this process recursively would be to 'unravel' an inverse representation of the tissue mechanics as a stiffness map, providing a pattern for the anisotropic weave. Both approaches have been reduced to practice and the intellectual property has been protected (patent pending).29 Tests are underway to determine the degree to which emergent properties are compromised by using the latter technique.

In summary, here we have demonstrated our novel protocol using SHIM in conjunction with TPEM to elucidate the organization and distribution of the collagen and elastin fibers of the periosteal sheath and to replicate nature's smart properties through creation of advanced materials via scale up of tissue architectures and multifunctional weaving. Inspired by nature's paradigms, this disruptive technology has significant implications for the development of next-generation advanced materials and mechanically functional textiles, including biomedical materials and even materials in transport and safety industries.

Methods

Sample Preparation (FIG. 2 and FIG. 4A-D)

Ovine studies were approved by and carried out in accordance with Institutional Animal Care and Use Committee protocol guidelines from the Canton of Grisons, Switzerland. To visualize and quantify bone perfusion, 0.8% procion red solution was intravenously injected (Imperial Chemical, London) at a dosage 0.01 µl/kg body mass 5 minutes prior to euthanasia Immediately after euthanasia, the femur, periosteum and surrounding muscle layer were resected and prepared for fixed, undecalcified histology using standardized protocols. The resulting polymethylmethacrylate embedded tissue blocks were sectioned transversely, every 500 µm, using a diamond wire saw (Wells Model 4240). After polishing to circa 100 µm (Buehler Automet 2000 Polisher), sections were mounted on glass slides with glass coverslips (Eukitt). To relate tissue fabric organization to prevalent mechanical loading histories, the major and minor centroidal axes of the bone cross-sectional area22,23 were calculated using the MomentMacroJ_v1_3 algorithm30 in Image J2 (NIH Image J2 v1.49). These quadrants were marked on the outer edges of the mounted bone specimens and served as reference points for high-resolution microscopy.

Figure 4E:
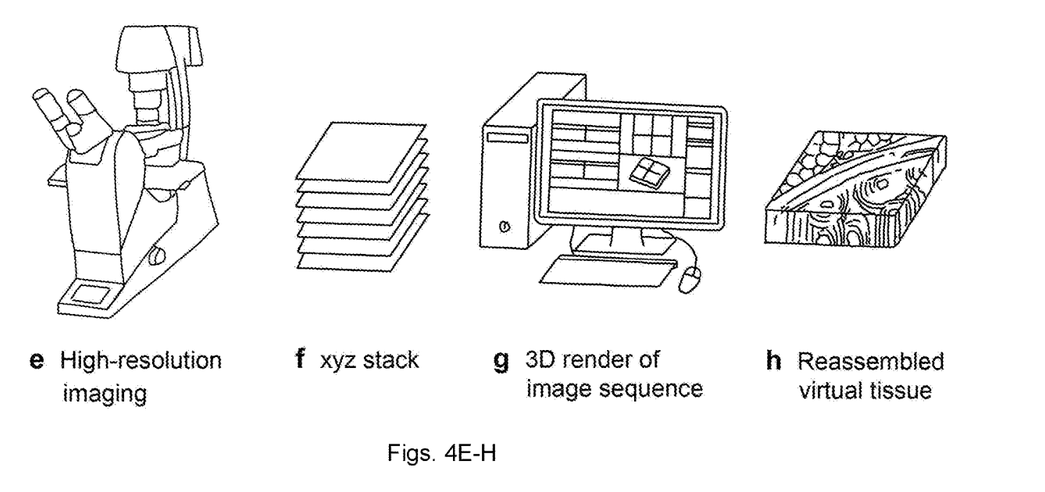
Figure 4I:
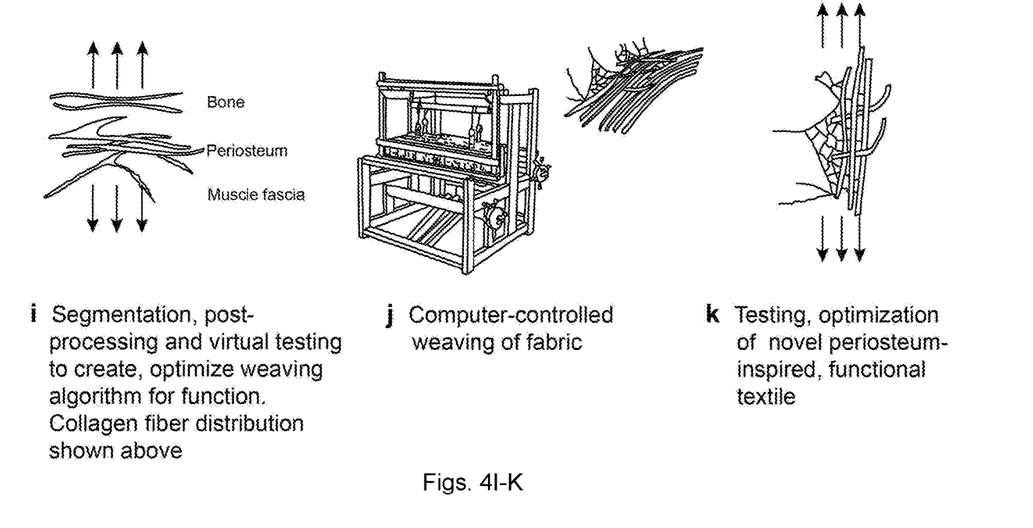

Imaging Protocol (FIG. 2 and FIG. 4E-F)

The specimens were imaged using a Leica SP5 II inverted microscope equipped with a Spectra Physics MaiTai HP DeepSea titanium sapphire multiphoton laser tuned to 830 nm (~100 fs pulse), a xyz high precision multipoint positioning stage and a 63× 1.3NA glycerol objective. The forward propagated second harmonic collagen signal was collected in the transmitted Non-Descanned-Detector using a 390-440 nm bandpass filter. The two-photon excitation of elastin was excited at 830 nm and collected in the photomultiplier tube (PMT) using a 435-495 nm emission filter. This filter was used to segment away autofluorescence that was observed in the green channel that did not completely correspond to elastin architecture. For the procion red signal, a 561 nm excitation was collected in the PMT using a 580-650 nm emission. A tiled scan was collected at the four quadrants correlating to the major and minor centroidal axis in the previously mentioned 3 channels, plus brightfield. Each 246 µm×246 µm tile was imaged at 12-bit with a scan speed of 100 Hz and a resolution of 2.081 pixels per micron. Within the tiled area, a high-resolution xyz stack, with a step size of 0.5 µm and a voxel size of 0.48 µm×0.48 µm×0.50 µm, was acquired to capture the distribution of collagen, elastin and vasculature of the specimens in three dimensional space.

Post-Processing and Modeling (FIG. 3 and FIG. 4G-I)

Both tiled images and xyz stacks were imported into Image J2 (NIH Image J2 v1.49), merged into a tiled overlapping image and converted into a .tif file. The image sequences from the xyz stacks were imported via separate channels into Mimics® (Materialise MIS Research18.0 Beta). The thresholds of the masks were determined by the intensity of the signal. Two masks were used to distinguish between strong and weak collagen and elastin signals. The lower threshold of the 'strong mask' was determined by the minimal intensity required to enable a mask with contiguous pixels that represent the features of the specimen. The lower threshold of the 'weak mask' was determined by minimizing noise in the specimen. For rapid prototyping, the masks were converted to .stl files and imported into a STL visualization software (Materialise 3-matic Research v10.0 Beta). Noise was removed from the models by filtering small shells up to 1 µm3 then re-converted into Binary STL files. The channels were then combined to create a composite model of the collagen, elastin and vascular architecture, which is completely scalable for subsequent rapid prototyping using novel multidimensional weaving algorithms.

Multidimensional Weaving of Scaled-Up Tissue Architectures Based on Nature's Paradigms (FIGS. 4j-k)

A recursive approach is used to prototype fabrics based on natural tissue weaves and fibers. Yarn fiber composition and stiffness gradients are achieved through scale up of natural fiber gradients and spinning. Weaves and higher order architectures are achieved using customized computer-aided weaving algorithms (ArahWeave) on a jacquard loom (AVL Looms) configured for complete control of every yarn woven into the fabric as well as through postprocessing after fabric weaving, analogous to posttranslational modification of extracellular matrix proteins.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A method of forming a substrate comprising:
   mapping a three dimensional spatial distribution of at least one structural protein fiber of extracellular matrix of biological material of interest comprising collagen fibers and elastin fibers, the three dimensional spatial distribution using second harmonic imaging microscopy of the collagen fibers and two photon excitation imaging microscopy of the elastin fibers to form individual tiles in a transverse x-y plane of an x-y-z coordinate system;

stacking the individual tiles in the z-direction to form a three-dimensional model;

designing a fiber assembly pattern comprising a weaving algorithm based on an intrinsic pattern of the at least one structural protein fiber of the extracellular matrix of the biological material in the three-dimensional model; and assembling fibers based on the fiber assembly pattern to form the substrate.

2. The method of claim 1, wherein the substrate is a biomedical material, tissue implant, or mechanically functional textile.

3. The method of claim 1, wherein the assembled fibers are woven using the weaving algorithm to define the weave pattern and fiber orientation.

4. The method of claim 1, wherein the biological material comprises tissue of a plant or animal.

5. The method of claim 4, wherein the tissue comprises at least one periosteum, pericardium, perimycium, or tissue spanning an organ or tissue compartment of animal or plant or other natural origin.

6. A method of forming a textile, the method comprising:

mapping a three dimensional spatial distribution of at least one structural protein fiber of extracellular matrix of biological material of interest comprising collagen fibers and elastin fibers, the three dimensional spatial distribution using second harmonic imaging microscopy imaging of the collagen fibers and two photon excitation imaging microscopy of the elastin fibers to generate individual tiles in a transverse x-y plane of an x-y-z coordinate system;

stacking the individual tiles in the z-direction to form a three-dimensional model;

designing a fiber assembly pattern comprising a weaving algorithm based on an intrinsic pattern of the at least one structural protein fiber of the extracellular matrix of the biological material in the three-dimensional model; and assembling fibers based on the fiber assembly pattern to form the textile.

7. The method of claim 6, wherein the textile is a tissue implant or mechanically functional textile.

8. The method of claim 6, wherein the assembled fibers are woven using the weaving algorithm to define the weave pattern and fiber orientation.

9. The method of claim 6, wherein the biological material comprises tissue of a plant or animal.

10. The method of claim 9, wherein the tissue comprises at least one of periosteum, pericardium, perimycium, or tissue binding an organ or tissue compartment of animal or plant or other natural origin.

11. A method of forming an engineered tissue construct, the method comprising:

mapping a three dimensional spatial distribution of collagen fibers and elastin fibers of the extracellular matrix of a tissue of interest, the three dimensional spatial distribution using second harmonic imaging microscopy imaging of the collagen fibers and two photon excitation imaging microscopy of the elastin fibers to generate individual tiles in a transverse x-y plane of an x-y-z coordinate system;

stacking the individual tiles in the z-direction to form a three-dimensional model;

designing a fiber weaving motif based on an intrinsic pattern of the collagen fibers and elastin fibers of the extracellular matrix of the tissue in the three-dimensional model; and weaving fibers based on the fiber weaving motif to define the weave pattern and fiber orientation and form the engineered tissue construct.

12. The method of claim 11, wherein the fiber assembly pattern comprises a weaving algorithm based on the intrinsic pattern.

13. The method of claim 12, wherein the tissue comprises at least one of periosteum, pericardium, perimycium, or tissue binding spanning an organ or tissue compartment.

14. The method of claim 1, wherein each tile has a thickness in the z-direction of 0.5 μm.

15. The method of claim 1, wherein the second harmonic imaging microscopy and the two photon excitation imaging microscopy are both performed at about 830 nm.

* * * * *